United States Patent [19]

Knöfel et al.

[11] Patent Number: 4,879,409

[45] Date of Patent: Nov. 7, 1989

[54] CYCLOALIPHATIC DIISOCYANATES, OPTIONALLY IN THE FORM OF ISOMERIC MIXTURES AND A PROCESS FOR THEIR PREPARATION

[75] Inventors: Hartmut Knöfel, Odenthal-Erberich; Michael Brockelt, Bergisch-Gladbach; Stefan Penninger; Herbert Stutz, both of Dormagen, all of Fed. Rep. of Germany

[73] Assignee: Bayer Aktiengesellschaft, Leverkusen, Fed. Rep. of Germany

[21] Appl. No.: 35,417

[22] Filed: Apr. 7, 1987

Related U.S. Application Data

[63] Continuation of Ser. No. 531,388, Sep. 12, 1983, abandoned.

[30] Foreign Application Priority Data

Sep. 22, 1982 [DE] Fed. Rep. of Germany ....... 3234996

[51] Int. Cl.[4] .............................................. C07C 69/00
[52] U.S. Cl. ................................................... 560/330
[58] Field of Search ........................................ 560/330

[56] References Cited

U.S. PATENT DOCUMENTS 3,361,814  1/1968  Campbell .
3,565,768  2/1971  Grant .
3,870,683  3/1975  Freure .

Primary Examiner—Alan Siegel
Attorney, Agent, or Firm—Gene Harsh; Joseph C. Gil

[57] ABSTRACT

A diisocyanate corresponding to the formula

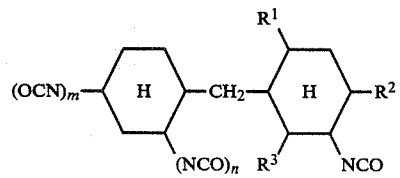

in which $R^1$, $R^2$, $R^3$, m and n are as defined herein is prepared by phosgenating a diamine corresponding to the formula

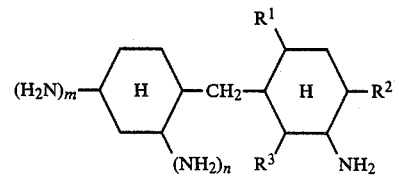

in which $R^1$, $R^2$, $R^3$, m and n are as defined herein. The diisocyanate may contain $C_1$–$C_{12}$-monoalkyl-substituted methylene-bis-(cyclohexylisocyanate)isomers in an amount of up to 40 wt. %. These new diisocyanates which are liquid at room temperature and compatible with polyols are particularly useful in the production of polyurethanes.

5 Claims, No Drawings

CYCLOALIPHATIC DIISOCYANATES, OPTIONALLY IN THE FORM OF ISOMERIC MIXTURES AND A PROCESS FOR THEIR PREPARATION

This application is a continuation, of application Ser. No. 531,388 filed Sept. 12, 1983 now abandoned.

BACKGROUND OF THE INVENTION

This invention relates to methylene-bis-(cyclohexyl isocyanates) which are mono-substituted on only one cyclohexane ring. The present invention also relates to a process for the preparation of such isocyanates.

Aliphatic and cycloaliphatic diisocyanates, such as hexamethylenediisocyanate, 3,5,5-trimethyl-1-isocyanato-3-isocyanatomethyl-cyclohexane and 4,4'-methylene-bis-(cyclohexylisocyanate) and mixtures of their position isomers and/or stereoisomers are used in polyurethane chemistry. For example, such diisocyanates may be used in the production of lightfast coating materials with good weather resistance. They may also be readily worked up into lacquer binders, elastomers or foams by a reaction with polyols if the diisocyanate is liquid at room temperature and compatible or sufficiently miscible with the polyols (see, e.g. German Offenlegungsschrift No. 1,768,832). Pure trans,trans-4,4'-methylene-bis-(cyclohexyl isocyanate), for example, is not suitable for this purpose because it is solid at room temperature (melting point 83° C.) and only slightly soluble in polyols. It is therefore removed from the reaction mixture by crystallization before the polyaddition reaction is completed. The stereoisomeric mixture of trans,trans-, cis,trans- and cis,cis-4,4'-methylene-bis-(cyclohexylisocyanate) (which may be obtained by hydrogenation of 4,4'-diaminodiphenylmethane on the nucleus followed by phosgenation) is also solid at room temperature since the trans,trans-diamine is the main product obtained when hydrogenation is carried out under normal conditions. Its usefulness for the production of the above-mentioned polyurethanes is therefore limited.

Although removal of the trans,trans-4,4'-methylene-bis-(cyclohexylisocyanate) from the stereoisomeric mixture is technically possible (e.g., by precipitation of the trans,trans-isomers in the form of carbamic acid chloride followed by filtration (see Japanese Patent Publication No. 53 046-944 of Apr. 27, 1978, this additional process step results in a reduction in isocyanate yield, which must be regarded as a serious disadvantage.

Liquid cycloaliphatic diisocyanates may be prepared according to the prior art by phosgenation of 2,4'-methylene-bis-(cyclohexylisocyanate) (see German Offenlegungsschrift No. 1,768,832). According to this Offenlegungsschrift, mixtures of 2,4'- and 4,4'-isomers are liquid even when the 2,4'-isomer content amounts to 30 to 95 wt % and the 4,4'-isomer has a trans-trans-isomer content of less than 50 wt %. It was found to be a disadvantage, however, that the 2,4'-isomer is difficult to obtain in the pure form since it is prepared in three stages (i.e., the condensation of aniline with formaldehyde, hydrogenation on the nucleus and phosgenation) and the 2,4'-diaminodiphenylmethane obtained at the stage of condensation only amounts to about 30% of the theoretical yield even under optimum conditions (see German Offenlegungsschrift No. 1,937,685). Consequently, a technically elaborate process of separation of isomers would be required to isolate the pure 2,4'-isomer.

The direct preparation of a methylene-bis-(cyclohexylisocyanate) rich in 2,4'-isomer by the phosgenation of a corresponding mixture of methylene-bis-(cyclohexylamine) isomers also has its disadvantages because the 2,4'-diaminodiphenylmethane content at the stage of aniline/formaldehyde condensation correlates with that of the 2,2'-isomer which is subject to a decomposition reaction at the stage of hydrogenation at the nucleus.

SUMMARY OF THE INVENTION

It is therefore an object of the present invention to provide new cycloaliphatic diisocyanates based on methylene-bis-(cyclohexylisocyanate) which are liquid at room temperature, satisfy the practical requirements with respect to solubility and compatibility with polyols and do not have the disadvantages of the present state of the art.

This and other objects which will be apparent to those skilled in the art are accomplished by phosgenating the diamine corresponding to the formula

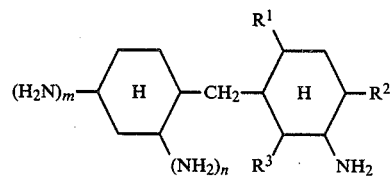

in which $R^1$, $R^2$, $R^3$, m and n are as defined below to form the corresponding diisocyanate.

DETAILED DESCRIPTION OF THE INVENTION

The present invention relates to diisocyanates corresponding to the general formula shown below, optionally in the form of isomeric mixtures and optionally mixed with up to 40 wt % (based on the total mixture) of other, optionally $C_1$-$C_{12}$-monoalkyl substituted, methylene-bis-(cyclohexylisocyanate) isomers:

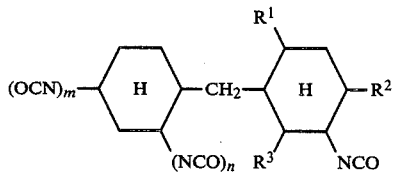

In the above formula, $R^1$, $R^2$ and $R^3$ may be the same or different with each radical representing hydrogen or a $C_1$-$C_{12}$-alkyl group (optionally branched), provided that two of these radicals are hydrogen and the third is an alkyl group of the type mentioned above, and n and m each represent 0 or 1 under the condition that the sum of m+n equals 1, and when m or n=0 the remaining free valency is saturated by hydrogen.

The present invention also relates to a process for the preparation of these diisocyanates or diisocyanate mixture, characterized in that diamines corresponding to the formula

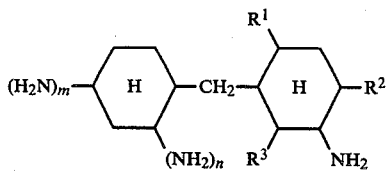

wherein $R^1$, $R^2$, $R^3$, m and n have the same meaning as indicated above, optionally in the form of a mixture of position and/or stereoisomers and optionally mixed with up to 40 wt % (based on the total mixture) of other $C_1$–$C_{12}$-monoalkyl-substituted methylene-bis-(cyclohexylamine) isomers, are phosgenated at temperatures from $-20°$ C. to $250°$ C.

The present invention also relates to the preparation of polyurethanes by the isocyanate polyaddition process from the diisocyanates of the present invention.

Starting materials for the process of the invention for preparing the new diisocyanates include diamines corresponding to the formula

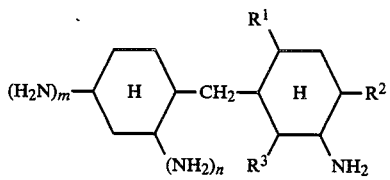

wherein $R^1$, $R^2$, $R^3$, m and n have the meaning indicated above but one of the groups $R^1$, $R^2$ or $R^3$ is preferably a $C_1$–$C_4$-alkyl group, in particular a methyl group, optionally in the form of a mixture of position and/or stereoisomers and optionally mixed with up to 40 wt % (based on the total weight of the mixture) of other $C_1$–$C_{12}$-monoalkyl-substituted methylene-bis-(cyclohexylamine) isomers.

The preferred diisocyanates of the present invention are those in which the alkyl groups have 1 to 4 carbon atoms, prreferably 1 carbon atom (methyl group).

Especially suitable diamines useful as starting materials for the process of the present invention are those diamines which correspond to the formula

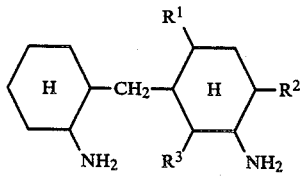

optionally in the form of position and/or stereoisomeric mixtures and optionally mixed with up to 40 wt % (based on the total mixture) of other $C_1$–$C_{12}$-monoalkyl-substituted methylene-bis-(cyclohexylamine) isomers, as well as diamines corresponding to the following formula

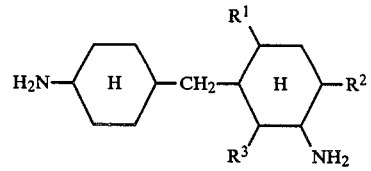

optionally present together with up to 40 wt %, preferably up to 30 wt % (based on the total weight of the mixture) of other $C_1$–$C_{12}$-monoalkyl substituted methylene-bis-(cyclohexylamine) isomers. The groups $R^1$, $R^2$ and $R^3$ in these formulae have the same meaning or preferred meaning already mentioned.

Basically, it may be said that the preferred starting materials include any diamines corresponding to the last two general formulae or any diamine mixtures whose main component or main components correspond to these formulae, with one of the groups $R^1$, $R^2$ or $R^3$ denoting an alkyl group having 1 to 4 carbon atoms, in particular a methyl group, the other said groups being hydrogen. The following are examples of the preferred or particularly preferred starting materials: 3,4'-diamino-4-methyl-dicyclohexylmethane, 3,2'-diamino-4-methyl-dicyclohexylmethane, 5,4'-diamino-2-methyl-dicyclohexylmethane, 5,2'-diamino-2-methyl-dicyclohexylmethane, 3,4'-diamino-2-methyl-dicyclohexylmethane, 3,2'-diamino-2-methyl-dicyclohexylmethane as well as isomeric mixtures with other position isomers in which these diamines constitute the main component. The corresponding ethyl-, propyl- or butyl-substituted diaminodicyclohexylmethanes and isomeric mixtures with other position isomers containing these compounds or mixtures thereof as their main component are also very suitable. In the context of the present invention, "main component" means that the diamine mixture contains at least 60 wt % of the components.

Preparation of the diamines or diamine mixtures to be used in the process of the present invention may be carried out by catalytic hydrogenation at the nucleus of the underlying aromatic diamines or by a two-stage catalytic hydrogenation of the underlying dinitro compounds which constitute the preliminary stage of the aromatic diamines. Preparation of these aromatic preliminary stages has been described, for example, in published European Patent Applications Nos. 0024665 and 0046556 and may be carried out by procedures analogous to the processes described in these publications. Thus the above-mentioned pure position isomers or diamine mixture containing these isomers as their main component may be prepared by condensation of p-nitrobenzyl chloride with p- or o-nitroalkylbenzenes, followed by a two-stage hydrogenation of the aromatic dinitro compounds. They may also be prepared by condensation of o-nitrobenzoyl chloride with p- or o-nitroalkylbenzenes, Clemmensen reduction and subsequent hydrogenation at the nucleus of the aromatic diamines obtained as intermediates.

Nuclear hydrogenation of the aromatic diamines is generally carried out by methods known in the art (see R. Rylander, Catalytic Hydrogenation in Organic Syntheses, Academic Press, New York, San Francisco, London (1979) page 190). In one such method, the aromatic diamines are catalytically hydrogenated until the uptake of hydrogen has been completed. Hydrogenation is carried out at $20°$ to $300°$ C. under a pressure of 20 to 300 bar, preferably at a temperature of from 100° to 300° C., in particular at 150° to 250° C. and under a pressure of 70 to 300 bar, in particular at 120 to 250 bar.

Hydrogenation may be carried out in the presence of from 0.1 to 30 wt %, preferably from 0.1 to 10 wt % (based on catalytically active metal and diamino compound) of a hydrogenation catalyst. Examples of suitable catalysts include elements of the 8th sub-Group of the Periodic System of Elements and catalytically active inorganic compounds of these elements, optionally applied to inert carriers such as active charcoal, silica gel or in particular aluminum oxide. Ruthenium, platinum, rhodium, nickel and/or cobalt catalysts, either in the form of their elements or in a chemically bound form, are particularly suitable. Ruthenium and catalytically active ruthenium compounds are particularly preferred. Specific examples of suitable ruthenium compounds include ruthenium dioxide; ruthenium tetraoxide; barium perruthenite; sodium, potassium, silver, calcium and magnesium ruthanate; sodium perruthenate; ruthenium pentafluoride; ruthenium tetrafluoride hydrate and ruthenium trichloride. When carrier substances are used for the catalysts, the metal content of the carrier catalyst is generally from 1 to 10 wt %, preferably from 1 to 5 wt %. The particular nature and quantity of the catalyst to be used is in no way critical to the invention.

It is often advantageous to carry out the hydrogenation reaction in the presence of ammonia because ammonia suppresses unwanted deamination reactions and the formation of secondary amines as by-products. If ammonia is used, it is generally added in quantities of from 0.1 to 30 wt %, preferably from 5 to 10 wt % (based on the quantity of starting materials to be hydrogenated).

The hydrogenation may be carried out solvent-free or in the presence of inert solvent. Low melting or liquid aromatic diamines are generally hydrogenated solvent-free whereas high melting diamines are hydrogenated in the form of solutions. Suitable solvents include organic compounds with a low boiling point which are inert under the reaction conditions, particularly alcohols such as methanol, ethanol, n-propanol and i-propanol, ethers such as dioxane, tetrahydrofuran and diethylether or hydrocarbons such as cyclohexane. Hydrogenation may be carried out continuously in a reaction tube or a cascade of pressure vessels, or, preferably, batchwise in a stirrer autoclave. In a batch process carried out in a stirrer autoclave, the catalyst, the substance to be hydrogenated and optionally solvent are introduced into the autoclave, the autoclave is repeatedly flushed with inert gas and ammonia is added, if desired. Hydrogen is then forced in under pressure and the mixture is heated to the reaction temperature and hydrogenation is carried out until constant pressure is obtained. Stirring is continued for a further period of about 0.5 to 5 hours at the same temperature. After cooling of the reaction mixture and separation of the catalyst, the hydrogenation product is generally worked up by distillation.

The hydrogenation products are obtained in high yields, generally amounting to over 90% of the theoretical yield, and may be freed from by-products such as amino-alkylbenzylcyclohexylamine by distillation. The hydrogenation products are often in the form of mixtures of position isomers and largely reflect the position isomerism of the starting materials. In addition, the cycloaliphatic diamines are generally mixtures of stereoisomers which, due to the asymmetric substitution of the underlying diamino-dicyclohexylmethane on only one cyclohexyl ring, are generally liquid at room temperature. Separation of such mixtures into individual position and/or stereo isomers is generally not necessary before use as starting materials in the practice of the present invention because isomeric purity is not required for this purpose. In fact, isomeric mixtures are frequently more desirable because they improve the properties of the diisocyanates.

Catalytic hydrogenation of the aromatic nitro compound is generally carried out in two stages according to U.S. Pat. No. 2,606,925, preferably in a low boiling alcohol (such as methanol, ethanol or isopropanol) and in the presence of from 0.1 to 10 wt % of a commercial ruthenium-aluminum oxide carrier catalyst containing 5 to 10 wt % of ruthenium. Reduction of the nitro group generally first takes place within a temperature range of 20° C. to 100° C. under a pressure of 1 to 150 bar whereas the subsequent hydrogenation on the nucleus takes place at 20° to 300° C. under a pressure of 20 to 300 bar, preferably at 100° to 300° C. under a pressure of 70 to 300 bar and most preferably at 150° to 250° C. under a pressure of 120 to 250 bar.

In the process of the present invention, phosgenation of the diamines or their salts exemplified above may be carried out by known methods in the presence of an inert organic solvent (see Houben-Weyl, Methoden der organischen Chemie, Georg Thieme Verlag Stuttgart (1952), Volume 8, 4th Edition, pages 120 et seq).

The salts to be phosgenated are preferably hydrochlorides or ammonium carbamates obtained by saturation of the diamine solutions with gaseous hydrogen chloride or carbon dioxide. Other salts which would also be suitable in principle are those obtained by neutralization of the diamines with acids which split off protons.

The selectivity of the phosgenation reaction depends to a large extent on the amine concentration and the excess of phosgene. The phosgene is preferably used in a high molar excess and the diamine to be phosgenated in a highly diluted form. The molar excess of phosgene generally amounts to 100 to 2000%, preferably 100 to 1000%. The amine concentration in the solution of amine to be phosgenated is generally from 0.1 to 15 wt %, preferably 5 to 10 wt %.

The solvents used may be any inert organic liquids or mixtures thereof having boiling points from 60° to 250° C. such as halogenated hydrocarbons, aromatic compounds, hydroaromatic compounds and their chlorinated compounds. Specific examples of such solvents include xylene, mesitylene, clorobenzene, dichlorobenzene, trichlorobenzene, chloronaphthalene and dichloroethane.

The reaction may be carried out either in a single stage by hot phosgenation at temperatures from 100° to 250° C. or in two stages by cold/hot phosgenation at temperatures from −20° to 250° C. under normal pressure.

When free amines are used as starting compounds (alkaline phosgenation), ammonium carbamic acid chloride is first prepared at temperatures from −20° to 60° C., and this is then reacted with phosgene at temperatures from 20° to 250° C. to form the diisocyanate.

A preferred method of carrying out the process is by dissolving the amines in a suitable organic solvent, precipitating them as ammonium carbamates by the introduction of carbon dioxide and treating the suspension with the theoretical quantity of phosgene at 0° to 50° C. The temperature is then slowly raised by further introduction of phosgene until a clear solution is obtained at temperatures from 100° to 180° C. Purification of the products of the process may be carried out after dephosgenation by evaporation of solvent followed by distillation at reduced pressure.

The products of the process of the present invention are obtained in high yields as colorless, low viscosity liquids and constitute valuable starting components for the production of polyurethanes by the isocyanate polyaddition process. The position and/or stereo isomerism of the diisocyanates reflects the isomerism of the diamines used for phosgenation. It is generally not necessary to separate the mixtures obtained by the process according to the invention into individual position and/or stereo isomers since the products according to the invention may be used directly for the purpose of the invention without such processes of separation. Herein lies one of the main advantages of the diisocyanates and diisocyanate mixtures according to the invention compared with the unsubstituted methylene-bis-(cyclohexylisocyanates) known in the art. The diisocyanates of the present invention are particularly advantageous for the production of polyurethane lacquers, polyurethane elastomers and polyurethane foams. In the known processes for producing such products, the diisocyanates of the present invention may be used instead of or together with the polyisocyanates hitherto employed.

The examples which follow serve to further illustrate the invention. All percentages given are percentages by weight unless otherwise indicated. Analysis of the distribution of isomers in the intermediate products and end products was carried out by gas chromatography.

EXAMPLES

Example 1

(1a) 250 g (1.18 mol) of 5,4'-diamino-2-methyldiphenyl methane were introduced into a 0.7 l refined steel autoclave together with 25 g of a ruthenium catalyst containing 5% ruthenium and aluminum trioxide as carrier. The unoccupied space above the contents of the autoclave was washed three times with nitrogen and hydrogen, and the autoclave was put under a pressure of 200 bar with hydrogen. The contents were then heated to 180° C. with stirring and hydrogenated at 200 bar until absorption of hydrogen ceases. After stirring for an additional 2 hours under the reaction conditions, the reaction mixture was cooled, the pressure in the autoclave was released, the product was taken up with methanol and the catalyst was filtered off. The catalyst was purified by washing with methanol, and the organic solutions were combined and the solvent evaporated off. The crude product was freed from higher boiling products by flash distillation at 0.1 mbar and subsequently purified by fractional distillation over a Vigreux column at 112° to 114° C./0.3 mbar. The yield of 5,4'-diamino-2-methyldicyclohexylmethane was 254.9 g (96.5% of theoretical yield).

(1b) 56 g (0.25 mol) of 5,4'-diamino-2-methyldicyclohexylmethane were dissolved in 700 ml of anhydrous chlorobenzene at room temperature, and a stream of dry carbon dioxide was passed in with vigorous stirring. A precipitate formed and the viscous suspension heated up to 40° C. This was cooled to 30° C. and 100 g of phosgene were rapidly introduced. The temperature rose to 45° C. The reaction mixture was then heated to 115° C. in the course of 2 hours and a further 300 g of phosgene were introduced during this time. A fall in viscosity took place and the precipitate dissolved completely. Stirring was continued for a further 3 hours at the same temperature and phosgene was introduced at the rate of 150 g per hour. The reaction mixture was then boiled under reflux for one hour with introduction of nitrogen, the solvent was distilled off at reduced pressure and the crude product was purified by distillation at 160° to 165° C./0.2 to 0.4 mbar. 59 g (82.7% of the theoretical yield) of 5,4'-diisocyanato-2-methyldicyclohexylmethane having an isocyanate content of 29.4%, a hydrolyzable chlorine content of 0.06% and a viscosity at 25° C. of 50 mPa.s were obtained.

EXAMPLE 2

The aromatic diamine mixture used in this Example was prepared by analogy to Example 7 of EP-A-0,024,665 by nitration of 4-methylbenzyl chloride, condensation with benzene, purification by recrystallization, renitration and reduction and working up of the product by distillation. When the aromatic diamine mixture had been further worked up as described below, it had the following composition:
2.4% of 2,2'-diamino-4-methyl-diphenylmethane,
31.3% of 3,2'-diamino-4-methyl-diphenylmethane,
64.5% of 3,4'-diamino-4-methyl-diphenylmethane and
1.8% of undefined diamines.

(2a) In a manner analogous to Example 1a, 250 g (1.18 mol) of the aromatic diamine mixture described above and 25 g of ruthenium-carrier catalyst (5% on $Al_2O_3$) were introduced into a 0.7 l stirrer autoclave and 25 g of ammonia were added after the autoclave had been flushed three times with nitrogen and hydrogen. Hydrogenation was then carried out at 108° C. and 200 bar with stirring. After removal of the catalyst and isolation of the reaction products by distillation at 120° to 122° C./0.1 mbar, 246 g (93.2% of theoretical yield) of a mixture of various diamino-4-methyl-dicyclohexylmethane isomers were obtained.

(2b) 112 g (0.5 mol) of the mixture of diamino-4-methyldicyclohexylmethane isomers prepared in Example 2a were dissolved in 1.4 l of anhydrous chlorobenzene at 50° C., and anhydrous carbon dioxide was then introduced with stirring until saturation point was reached. The resulting suspension was cooled to 10° C. and 200 g of phosgene were introduced. The reaction mixture was then slowly heated with further introduction of 300 g of phosgene until the solid substance dissolved completely at 120° C. Phosgenation was continued for an additional 3 hours under the same conditions. The reaction mixture was then boiled under reflux for one hour and excess phosgene was driven off with nitrogen. The crude product was concentrated and distilled at 158° to 165° C./0.1 mbar. 124 g (89.3% of theoretical yield) of a mixture of various diisocyanato-4-methyl-dicyclohexylmethane isomers distilled over in the process. This mixture had an isocyanate content of 30.2%, a hydrolyzable chlorine content of 0.06% and a viscosity at 25° C. of 40 mPa.s.

EXAMPLE 3

(3a) A diamine mixture having the composition indicated below was prepared in a manner analogous to Example 10 of EP-A 0,024,665 by dinitration of a condensate of 2-methyl-benzyl chloride and benzene, followed by hydrogenation of the resulting dinitro compound. Compositon:

1% of 6,2'-diamino-2-methyl-diphenylmethane, 14,5% an isomer mixture of 3,2'- and 5,2'-diamino-2-methyl-diphenylmethane, 0,9% of 6,3'-diamino-2-methyl-diphenylmethane, 7,9% of an isomer mixture of 4,2'- and 6,4'-diamino-2-methyldiphenylmethane, 75% of an isomeric mixture containing more than 80% of 3,4'- and 5,4'-diamino-2-methyldiphenylmethane, the remainder consisting of other diamino-2-methyl-diphenylmethanes, and 0.7% of undefined polyamines. 250 g (1.18 mol) of this diamine mixture were hydrogenated in accordance with the procedure described in Example 1a) within 9.5 hours at 180° C. and 200 bar in the presence of 25 g of ruthenium catalyst (5% Ru on $Al_2O_3$) and 25 g of ammonia. After release of pressure from the autoclave, the product was taken up with methanol, the catalyst was removed by filtration and the solvent was evaporated off. After fractional distillation, 221.5 g of a mixture boiling at 100° to 108° C./0.1 mbar, consisting of various diamino-2-methyldicyclohexylmethane isomers containing traces of deaminated product and half hydrogenated diamino-methyldicyclohexyl methane were obtained.

(3b) 250 g of phosgene were condensed in 700 ml of chlorobenzene at 0° to 8° C. A solution in 700 ml of chlorobenzene of 112 g (0.5 mol) of the diamine prepared in 3a) were added dropwise at this temperature with stirring. The reaction mixture was then heated to the reflux temperature with introduction of 150 g of phosgene per hour and stirring was continued for an additional 3 hours under the same conditions. After dephosgenation and removal of the solvent by distillation, the product was purified by flash distillation at 164° to 168° C./0.2 to 0.3 mbar. 118.6 g (84.2% of theoretical yield) of various diisocyanato-2-methyldicyclohexylmethane isomers were obtained (NCO content: 29.8%, hydrolyzable chlorine content: 0.1%, viscosity/25° C.: 45 mPa.s).

EXAMPLE 4

(4a) 250 g (1.18 mol) of 3,4'-diamino-4-methyl-diphenylmethane and 25 g of Ru/$Al_2O_3$ catalyst (5% Ru) were introduced into a 0.7 l stirrer autoclave. The autoclave was flushed three times with nitrogen and hydrogen, 25 g of ammonia were introduced, the autoclave was put under a hydrogen pressure of 200 bar and the mixture was heated to 180° C. with stirring. After complete hydrogen absorption followed by stirring for two more hours, the autoclave contents were cooled to room temperature and the autoclave pressure was released. The catalyst was removed by filtration and washed and the combined organic phases were worked up by distillation. 250 g (94.6% of theoretical yield) of 3,4'-diamino-4-methyl-dicyclohexylmethane (Bp: 125°–126° C./0.1 mbar) were obtained. The elemental analysis of the product was as follows: $C_{14}H_{28}N_2$ (224.40)

| Calculated: | C | 74.9% | H | 12.6% | N | 12.5% |
|---|---|---|---|---|---|---|
| Found: | C | 74.8% | H | 12.8% | N | 12.3% |

(4b) 175 g (0.78 mol) of 3,4'-diamino-4-methyl-dicyclohexylmethane were dissolved in 2 l of anhydrous chlorobenzene, and anhydrous carbon dioxide was introduced at 40°–45° C. until saturation was reached. The resulting suspension was cooled to about 20° C. and 200 g of phosgene were introduced with stirring and cooling so that the temperature remained constant. As phosgene continued to be introduced at the rate of 100 g/hour, the mixture became heated until at about 110° C. the precipitate had completely dissolved. Stirring was continued for 2 more hours under constant conditions and the reaction mixture was dephosgenated by boiling it under reflux for one hour with introduction of nitrogen. The solvent was distilled off at reduced pressure. The crude product was distilled at 165° C./0.5 mbar, leaving a residue of 5.5 g. 201 g (93.4% of theoretical yield) of 3,4'-diisocyanato-4-methyl-dicyclohexylmethane with an isocyanate content of 30.4% and a hydrolyzable chlorine content of 0.01% were obtained.

EXAMPLE 5

(5a) 500 g (2.36 mol) of the diamine mixture described in Example 8c) of EP-A 024,665 were introduced into a 1.3 l stirrer autoclave. This diamine mixture boiled at 150° to 200° C./0.133 mbar and was composed of 34,5% of 3,4'-diamino-4-methyl-diphenylmethane, 16,9% of 5,4'-diamino-2-methyl-diphenylmethane, 7,2% of 3,4'-diamino-2-methyl-diphenylmethane, 15,2% of 3,2'-diamino-4-methyl-diphenylmethane, 7,5% of 5,2'-diamino-2-methyl-diphenylmethane, 3,2% of 3,2'-diamino-2-methyl-diphenylmethane and 15,5% of diamino-methyl-diphenylmethane of unknown isomer distribution.

After the addition of 50 g of a ruthenium/aluminium oxide carrier catalyst containing 5% of ruthenium and rinsing the autoclave three times with nitrogen and hydrogen, 50 g of ammonia were added. Hydrogen was introduced to a pressure of 200 bar and the reaction mixture was heated with stirring to 180° C. Hydrogenation was carried out at 200 bar until constant pressure was obtained after 2 hours. Stirring was continued for 2 more hours, the autoclave contents were cooled to room temperature and the pressure was released. The crude product, taken up with methanol, was freed from catalyst by filtration and purified by distillation. A yield of 497.6 g (94.2% of theoretical yield) of a mixture of various diaminomethyl-dicyclohexylmethane isomers was obtained as main fraction boiling at 110° to 115° C./0.133 mbar. The compositon of this mixture substantially corresponded to the aromatic diamine mixture described above.

(5b) 224 g of the diamine mixture prepared in Example (5a) were dissolved in 2 l of anhydrous chlorobenzene, and carbon dioxide was introduced with stirring until saturation was reached. The resulting suspension was cooled to 20° to 40° C. and then heated to 120° C. with introduction of phosgene at the rate of 100 g per hour.

A clear solution was obtained from 100° C. onwards. After 2 more hours of stirring under the same conditions, the introduction of phosgene was stopped and the reaction mixture was dephosgenated by boiling it under reflux for one hour and at the same time blowing nitrogen through. The solvent was then distilled off at reduced pressure and the crude isocyanate was purified by distillation at 145° to 155° C./0.1 mbar. The yield of diisocyanate mixture which had an isocyanate content of 30.4% and a hydrolyzable chlorine content of 0.05% and an isomeric composition substantially corresponding to that of the starting product amounted to 262 g (94.9% of theoretical yield).

EXAMPLE 6

(6a) Following the procedure of example 5a) a diamine mixture obtained in accordance with example 5 of EP-A 46556 composed of 1,9% of a mixture of 2,2'-diamino-4- and 2,2'-diamino-6-ethyl-diphenylmethane, 11,1% of 4,2'-diamino-2-ethyl-diphenylmethane, 20,1% of a mixture of 3,2'-diamino-2-, 3,2'-diamino-4- and 5,2'-diamino-2-ethyl-diphenylmethane, 66,1% of a mixture more than 80% of which consisted of 3,4'-diamino-4- and 5,4'-diamino-2-ethyl-diphenylmethane and the remainder of which consisted of other diamino-ethyl-diphenylmethanes of unknown isomer distribution and 0,8% unknown triamines was hydrogenated. After working up of the hydrogenation product by distillation a diamine mixture boiling at 115°–119° C./0,1 mbar is obtained 99% of which consisted of diamino-ethyl-dicyclohexyl-methane isomers the isomer distribution of which corresponded to the isomer distribution of the starting material.

(6b) 160 g of the hydrogenated diamine mixture of example (6a) were dissolved in 2 l of chlorobenzene. The solution is saturated with carbon dioxide to yield a suspension of solids. The suspension of solids thus obtained was treated at a maximum temperature of 10° C. with 250 g of phosgene under stirring. Subsequently the reaction mixture was heated to reflux temperature and kept at this temperature for 5 hours under continuous introduction of phosgene. Finally the phosgenation product was worked up by distillation to yield 165 g (85,5% of the theory) of a mixture of diisocyanato-ethyl-dicyclohexyl-methane isomers boiling at 138°–145° C./0,1 mbar having an NCO-content of 28,3% and a viscosity of 48 mPa.s/25° C. and an isomer distribution which corresponded to the isomer distribution of the starting diamine mixture.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate corresponding to the formula

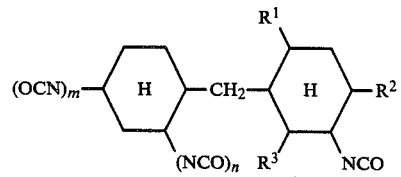

in which $R^1$, $R^2$ and $R^3$ may be the same or different with each radical representing hydrogen or a $C_1$–$C_{12}$ alkyl group, provided that two of the radicals $R^1$, $R^2$ and $R^3$ represent hydrogen and the third radical represents an alkyl group, and n and m each represent 0 or 1, provided that the sum of m+n equals 1 and when m or n=0, the free valency is saturated by hydrogen and in which $C_1$–$C_{12}$-monoalkyl-substituted methylene-bis-(cyclohexylisocyanate)-isomers may be present in the diisocyanate in an amount of up to 40 wt %.

2. The diisocyanate of claim 1 corresponding to the formula

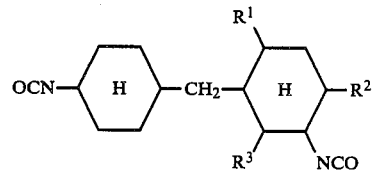

in which $R^1$ or $R^2$ or $R^3$ represents an alkyl group having 1 to 4 carbon atoms.

3. The diisocyanate of claim 2 in which $R^1$ or $R^2$ or $R^3$ represents a methyl group.

4. The diisocyanate of claim 1 corresponding to the formula

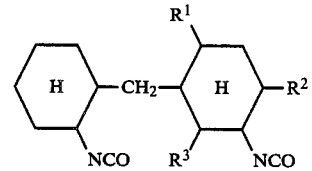

in which $R^1$ or $R^2$ or $R^3$ represents an alkyl group having 1 to 4 carbon atoms.

5. The diisocyanate of claim 4 in which $R^1$ or $R^2$ or $R^3$ represents a methyl group.

* * * * *